(12) United States Patent
Smith

(10) Patent No.: US 6,783,562 B2
(45) Date of Patent: Aug. 31, 2004

(54) NONWOVEN ABRASIVE COMPOSITE

(75) Inventor: Howell N. Smith, Mt. Juliet, TN (US)

(73) Assignee: Reemay, Inc., Old Hickory, TN (US)

( * ) Notice: Subject to any disclaimer, the term of this patent is extended or adjusted under 35 U.S.C. 154(b) by 0 days.

(21) Appl. No.: 10/154,239

(22) Filed: May 22, 2002

(65) Prior Publication Data

US 2003/0217516 A1 Nov. 27, 2003

(51) Int. Cl.[7] ............................. B24D 11/00; B24D 3/00
(52) U.S. Cl. ............................ 51/298; 51/293; 51/295; 51/297
(58) Field of Search .......................... 51/293, 295, 297, 51/298; 451/533, 539; 442/382, 389

(56) References Cited

U.S. PATENT DOCUMENTS

| 4,078,340 A | 3/1978 | Klecker et al. |
| 4,225,321 A | 9/1980 | Swiatek |
| 4,386,943 A | 6/1983 | Gümbel et al. |
| 4,780,361 A | 10/1988 | Schlein |
| 5,084,326 A | 1/1992 | Vöhringer |
| 5,213,588 A | 5/1993 | Wong et al. |
| 5,578,362 A | 11/1996 | Reinhardt et al. |
| 5,919,549 A * | 7/1999 | Van et al. .................. 428/141 |
| 6,177,370 B1 | 1/2001 | Skoog et al. |
| 6,302,930 B1 | 10/2001 | Lux |

FOREIGN PATENT DOCUMENTS

| WO | WO 97/49326 A | 12/1997 |
| WO | WO 00/64326 A | 11/2000 |
| WO | WO 01/87543 A | 11/2001 |

OTHER PUBLICATIONS

International Search Report 8/03.

* cited by examiner

*Primary Examiner*—Michael Marcheschi
(74) *Attorney, Agent, or Firm*—Alston & Bird LLP

(57) ABSTRACT

A nonwoven composite cleaning pad is disclosed. The cleaning pad includes a first nonwoven layer having an absorbent surface. A second nonwoven layer is laminated to the first layer, and a plurality of abrasive polymer formations are provided on the exposed surface of the second layer.

12 Claims, 3 Drawing Sheets

NONWOVEN ABRASIVE COMPOSITE

BACKGROUND OF THE INVENTION

The present invention is related to nonwoven composite materials. More particularly, the invention relates to a composite sheet material that is soft and absorbent on one side, and relatively abrasive on the other side. The nonwoven composite material has properties that make it suitable for use as a cleaning scrub pad and wipe.

Various types of nonwoven abrasive products have been used in the cleaning industry. For example, U.S. Pat. No. 4,227,350 discloses an abrasive product comprising a uniform lofty web of continuous three-dimensionally bonded polyamide filaments. Similarly, U.S. Pat. No. 4,078,340 discloses an abrasive pad comprising a lofty fibrous nonwoven structure of mixed denier nylon or polyester crimped fibers, which are bonded together with a binder that contains finely divided abrasive particles. These types of abrasive cleaning pads are preferably used for cleaning various surfaces, such as removing paint, grease, dirt, or other surface coatings, or preparing surfaces for painting or other coating operations.

Conventional cleaning pads such as these and others known in the art have the difficult task of providing sufficient abrasiveness to the work surface, yet cannot be damaging thereto. Certain materials can be overly abrasive to the work surface, and thus cleaning pads made from these materials have limited use. Many cleaning pads are also relatively expensive to manufacture, particularly if natural fibers are used. Manufacturing cost is further compounded if more than one type of material is used in the cleaning pad, such as in the pads mentioned above. In particular, the materials used in the cleaning pad may be difficult to attach and/or maintain together, so expensive manufacturing techniques and materials may be required. Attaching the abrasive materials to the pad can also add cost, as expensive binder resins may be required, which also add complexity to the manufacturing operation. Accordingly, there is a need for a cleaning pad, such as to be used for cleaning and wiping surfaces, that is easy and inexpensive to manufacture, yet can be used on a wide variety of work surfaces without scratching.

BRIEF SUMMARY OF THE INVENTION

The present invention provides a nonwoven composite cleaning pad that comprises two nonwoven layers laminated together. According to one embodiment, the first nonwoven layer has an absorbent surface, and the second layer has a plurality of abrasive polymer formations on the exposed surface. Advantageously, the first and second layers are nonwoven materials, which are relatively inexpensive to manufacture and can be easily bonded together. In addition, the nonwoven materials are selected to provide one side that is relatively abrasive, such as for scrubbing surfaces, while the other side is soft and absorbent in order to retain water and be able to wipe up any liquid or particles after scrubbing.

More specifically, in one embodiment of the present invention one of the nonwoven layers is a nonwoven structure comprising hydrophilic staple fibers. For example, the nonwoven structure may be a carded nonwoven web formed of a blend of polypropylene fibers and rayon fibers. In one particularly advantageous embodiment, the nonwoven web is formed of about 80% polypropylene fibers and about 20% rayon fibers. The nonwoven web presents a soft absorbent surface. Regardless of the fiber composition, the fibers can be bonded to one another at discrete points according to a predetermined pattern in order to add strength to the web.

The other nonwoven layer is preferably formed of continuous filaments. More particularly, the nonwoven layer is preferably a spunbond nonwoven web formed of substantially continuous filaments. In one embodiment, the nonwoven layer comprises a polyester spunbond nonwoven web of trilobal filaments having a basis weight of at least about 2.0 oz./yd$^2$. Advantageously, both layers comprising the cleaning pad of the present invention are nonwoven materials, which makes the cleaning pad easier to manufacture and less expensive as well.

The cleaning pad of the present invention also includes a plurality of abrasive polymer formations applied to the exposed surface of the second layer. According to one embodiment, the abrasive formations are formed of a thermoplastic polymer, such as polyester. The degree of abrasiveness can be controlled by altering the melt viscosity of the polymer composition and/or the size, spacing or shape of the polymer formations.

A method of manufacturing a nonwoven composite is also described, wherein a first nonwoven layer is provided having an absorbent surface. According to one embodiment, a second nonwoven layer is laminated to the first layer, and a plurality of abrasive polymer formations are provided on the surface of the second layer. The polymer formations are applied using a heated roll, which is preferably engraved with a predetermined pattern of indentations.

Accordingly, the cleaning pad of the present invention is easier to manufacture and maintains its integrity compared to conventional cleaning pads. Advantageously, the composite preferably comprises two web-like layers made from 100% nonwoven materials, which eases manufacturing and reduces cost. The nonwoven materials are easily adhered to one another, such as with standard lamination processes known in the art. The polymer formations on the surface of one of the layers of the cleaning pad provide a relatively abrasive surface, yet will not scratch, such that the pad can be used to clean a wide variety of surfaces, such as marble, glass, plastic, ceramic, Teflon®, and the like. As such, consumers can use the composite of the present invention without fear of damaging the particular work surface. The cleaning pad of the present invention can also be used as a personal care article, such as an exfoliating scrub pad or wipe.

BRIEF DESCRIPTION OF THE SEVERAL VIEWS OF THE DRAWINGS

Figure 1:
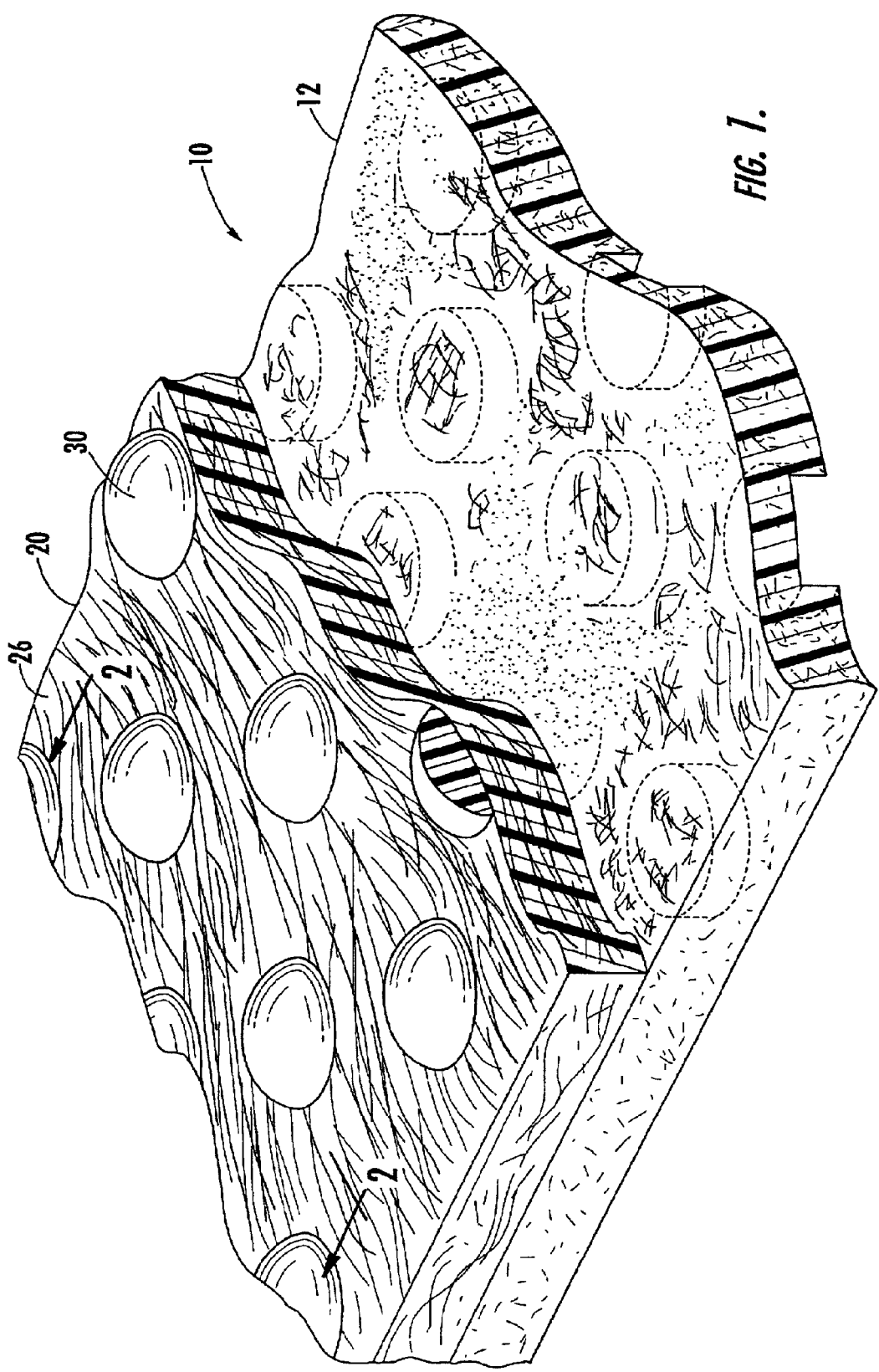
Figure 2:
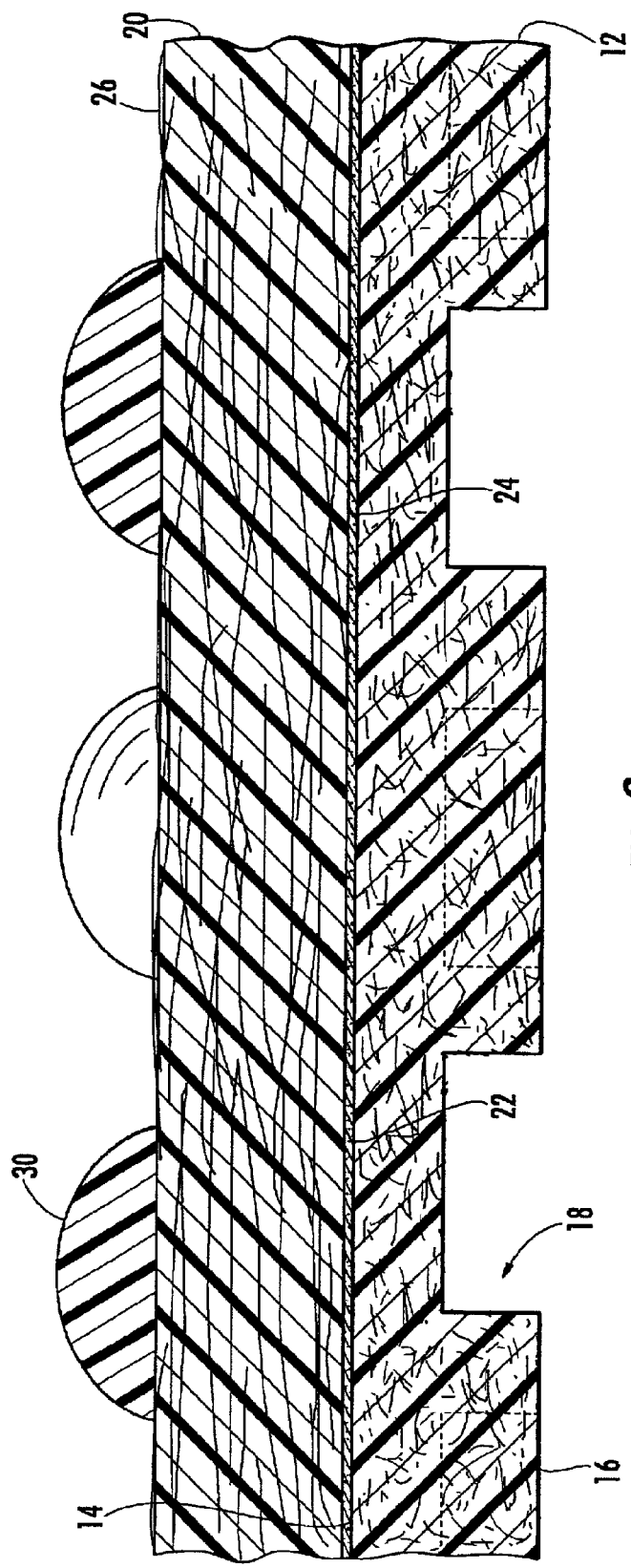
Figure 3:
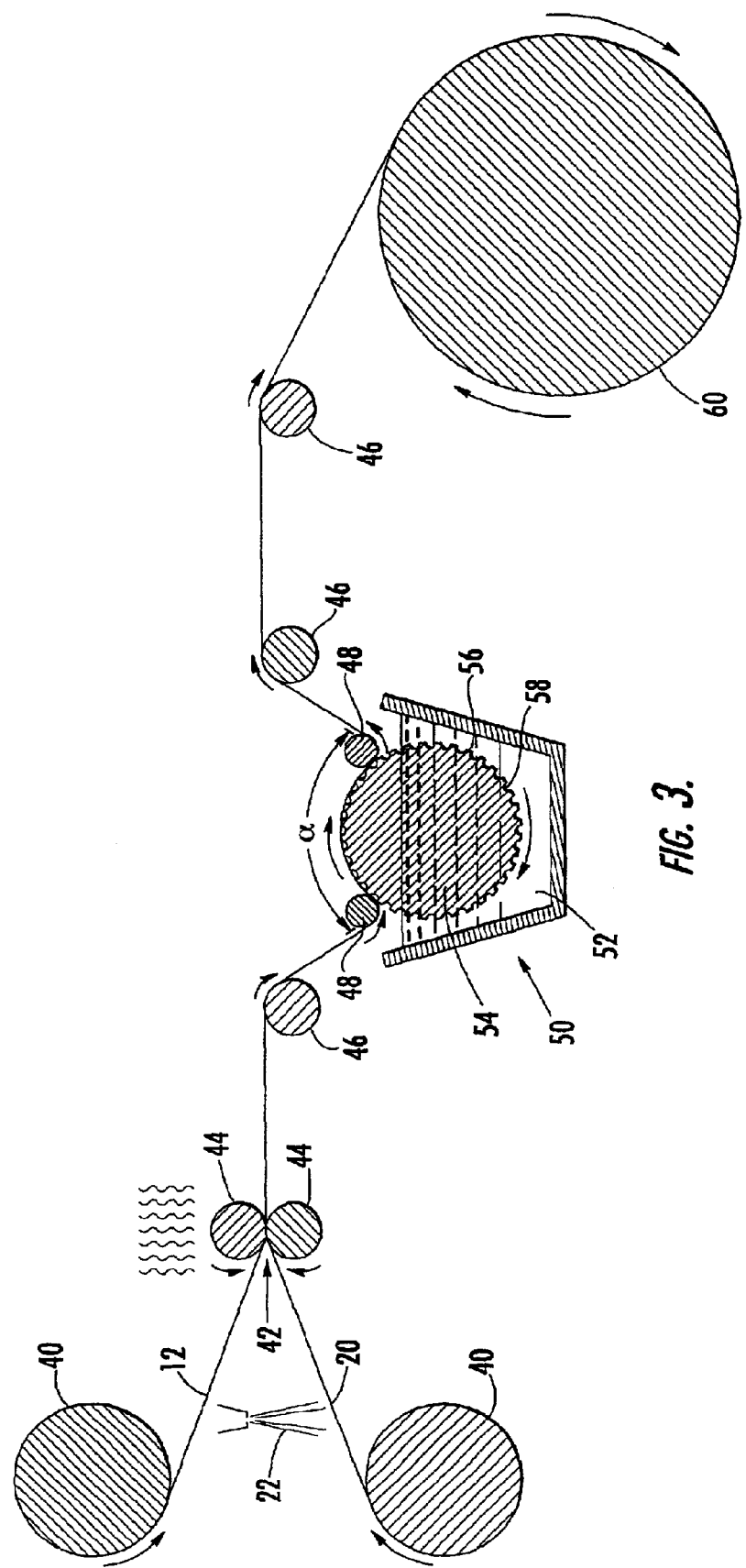

Having thus described the invention in general terms, reference will now be made to the accompanying drawings, which are not necessarily drawn to scale, and wherein:

FIG. 1 is a perspective cutaway view of a nonwoven composite according to one embodiment of the present invention;

FIG. 2 is a cross-sectional view of a nonwoven composite as shown along lines 2—2 of FIG. 1; and FIG. 3 is an illustration of an exemplary process for making a nonwoven composite according to one embodiment of the present invention.

DETAILED DESCRIPTION OF THE INVENTION

The present invention now will be described more fully hereinafter with reference to the accompanying drawings, in which preferred embodiments of the invention are shown.

This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

FIG. 1 is a perspective view of a nonwoven composite cleaning pad 10 according to one embodiment of the present invention. In particular, the cleaning pad 10 includes a layer 12 that is relatively absorbent. Another nonwoven layer 20 is attached to the absorbent layer 12 to form a composite nonwoven structure, and a plurality of abrasive polymer formations 30 in the form of particles or bumps extend from the exposed surface 26 of the nonwoven layer 20. The cleaning pad 10 is particularly advantageous because it can be used to clean a wide variety of surfaces, such as marble, plastic, glass, ceramic, Teflon®, and the like, without scratching. The cleaning pad 10 can also be used as a wipe for absorbing moisture and capturing particles removed during cleaning. In this regard, either side of the pad 10 can be used to clean surfaces, but the abrasive formations 30 provide a more aggressive surface than the absorbent layer 12.

In the embodiment shown in FIGS. 1 and 2, the absorbent layer 12 includes hydrophilic staple fibers, and preferably includes a carded blend of at least two different fibers to form the nonwoven structure. Examples of suitable hydrophilic staple fibers include rayon, cotton, and regenerated cellulose. The remaining fibers may be formed from non-hydrophilic fibers, preferably thermoplastic fibers of polypropylene, polyethylene terephthalate, or other suitable polymer. The absorbent layer 12 may be formed entirely from hydrophilic staple fibers, or the hydrophilic fibers may be blended with the non-hydrophilic fibers in any ratio to attain the desired absorbency or "holding capacity" of the absorbent layer 12. The presence of thermoplastic fibers in the blend allows for bonding the fibers into a coherent, strong web by thermal bonding. In one embodiment where the absorbent layer 12 includes rayon and polypropylene staple fibers, increasing the percentage of rayon increases the absorbency of the layer 12. However, rayon and similar fibers are often more expensive than polypropylene, and thus a high ratio of rayon fibers can result in an increased production cost of the cleaning pad 10. In a preferred embodiment, the absorbent layer 12 includes rayon and polypropylene staple fibers that are blended in a ratio of about 80% polypropylene/20% rayon.

The absorbent layer 12 has opposing sides 14, 16, and defines a plurality of cavities 18 in the side 16 and extending at least partially through the layer 12. The cavities 18 are formed by a conventional thermal bonding process, which helps bond the staple fibers and thus strengthen the layer 12. In particular, the cavities 18 are the result of a "point bonding" or "pattern bonding" process, whereby discrete bond points or zones are separated from one another by unbonded areas or zones. In one embodiment, the point bonding is performed using a heated calender roll with a diamond pattern. Point bonding and pattern bonding are often utilized for applications in which it is desired to preserve the softness of the fabric. These types of bonding are distinguished from "area bonding," whereby fiber bonds are not separated by unbonded areas, but instead are found throughout the area of the fabric. Because of the larger number of fiber-to-fiber bonds, area bonded fabrics are typically stronger than a point bonded fabric and are also less soft and less flexible. The cavities 18 also add to the surface area of the side 16, which creates more contact area for absorbing liquids. The web may be treated with a surfactant for enhanced absorbency.

The nonwoven layer 20 is attached to the absorbent layer 12 by any suitable method, such as by laminating the layers together using an adhesive layer 22. The adhesive layer may, for example, be a powdered acrylic adhesive that is melted between the layers during manufacturing of the cleaning pad 10, as discussed below. The adhesive layer could also be in the form of a film or a scrim or a meltblown web of hot-melt adhesive. In particular, the adhesive layer 22 is interposed between the side 14 of the absorbent layer 12 and the side 24 of the nonwoven layer 20. Alternatively, the two layers may be bonded together without an adhesive by thermal point bonding or ultrasonic bonding.

The nonwoven layer 20 can be formed from a variety of nonwoven materials, but according to one embodiment the layer comprises a spunbond nonwoven web formed of polyester continuous filaments. Spunbond nonwoven fabrics are formed by extruding molten thermoplastic material as continuous filaments from a plurality of fine capillaries of a spinneret. The filaments preferably have a trilobal cross-section. Other cross-sectional configurations, such as circular or multilobal cross-sections, can be employed if desired. The filaments are drawn and then randomly deposited onto a collecting surface. The filaments are bonded to form a coherent web.

The nonwoven layer 20 should have a basis weight of at least about 2.0 oz/yd$^2$, and preferably about 2.9 oz/yd$^2$. One specific example of a suitable nonwoven fabric possessing the required levels of strength is a product sold under the trademark Reemay® by BBA Nonwovens. This product is a spunbonded nonwoven fabric made from fibers in the form of substantially continuous filaments of polyester. The freshly extruded filaments are attenuated using pneumatic jets or slow-draw attenuators and have a denier per filament of from about 4 to about 6. The filaments are bonded to one another to form a nonwoven sheet material having excellent strength characteristics. The filaments include a blend of homopolyester matrix filaments and copolyester binder filaments. The polymer composition may also include suitable additives, stabilizers, and antioxidants.

The abrasive polymer formations 30 are applied to the exposed surface 26 of the nonwoven layer 20 forming protuberances extending therefrom. In one embodiment, the polymer formations 30 are formed from polyester and are adhered to the exposed surface of the nonwoven layer 20 in a predetermined uniform pattern. Various other polymers could be employed, such as nylon, polypropylene or acrylic for example. The polymer formations 30 can have uniform size, shape, and abrasiveness. The shapes of the polymer formations 30 are shown as being spherical or rounded, but other alternative shapes could be selected instead. However, the somewhat rounded shapes of the formations 30 as shown in FIGS. 1 and 2 are advantageous because no sharp edges are present that could scratch a work surface.

FIG. 3 shows an exemplary process for making a nonwoven composite cleaning pad according to one embodiment of the present invention. As shown in FIG. 3, the absorbent layer 12 and the nonwoven layer 20 are directed toward one another from let off rolls 40. The absorbent layer 12 has a pattern of spaced-apart depressions or cavities 18 resulting from thermal point bonding by a patterned calender roll. In the embodiment shown in FIG. 3, the depressions or cavities 18 of the absorbent layer 12 are facing away from the nonwoven layer 20. The adhesive layer 22 in powdered form is applied to at least one of the layers, and the layers are advanced to a nip 42 between opposing rolls 44. At least one of the opposing rolls 44 is heated. The powdered adhesive melts to form the adhesive layer 22, which securely holds the layers together. In particular, the absorbent layer 12 and the nonwoven layer 20 are not subject to delamination, but instead are structurally combined with one another to form a composite material.

The laminate composite is advanced over at least one roll 46 to an applicator 50. The applicator 50 includes an engraved roll 54 that is partially submerged in a bath of molten polymer 52 that forms the abrasive formations 30 shown in FIGS. 1 and 2. More specifically, the laminate composite is advanced between two tension rolls 48 and into contact with the outer surface 56 of the embosser roll 54 along an arcuate path defined by an angle α, which preferably is about 30°. A plurality of indentations 58 (greatly enlarged in FIG. 3 for clarity) is defined in the outer surface 56 of the roll 54, which preferably is formed of steel. As the roll rotates about its longitudinal axis, the indentations 58 capture the molten polymer and carry the polymer towards the laminate composite, wherein the polymer cools and begins to solidify once the polymer captured in the indentations exits the bath. Accordingly, the laminate composite contacts the roll 54 and the polymer-filled indentations 58 transfer the solidifying polymer to the exposed outer surface 26 of the nonwoven layer 20 such that the polymer is adhered to the nonwoven layer and forms the abrasive formations 30.

Advantageously, the size, shape, and abrasiveness of the formations 30 can be altered by appropriate selection of the polymer and its rheological properties. For example, by using a polymer with a relatively low melt viscosity, the molten polymer will tend to flow more and form relatively smooth, rounded formations. As the melt viscosity is increased, the polymer will tend to flow less before solidifying, thus more sharply defined formations. More viscous, molten polymers will produce formations with sharply defined surfaces or "peaks" as the web separates from the applicator roll. Alterations in the abrasiveness can also be effected by changing the pattern, spacing and size of the indentations 58 in the roll 54.

The laminate composite with the abrasive formations 30 is then advanced along a series of rolls 46 to a take-up roll 60. Although not shown for clarity, other rolls and processes may be included, such as engaging the laminate composite against a chiller roll to assist in cooling the abrasive formations 30.

Accordingly, the cleaning pad 10 of the present invention provides at least two layers 12, 20 of nonwoven material, which results in a cleaning pad that is easier to manufacture, maintains its structural integrity longer, and is less expensive to manufacture compared to conventional cleaning pads, particularly cleaning pads that include sponge material. The abrasive polymer formations 30 will not scratch the work surface, so that the cleaning pad 10 can be used on a variety of surfaces without fear of damage from scratches. In addition, the absorbent layer 12 allows moisture or liquid to be absorbed, so that the pad 10 can be used as a wipe as well.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A nonwoven composite cleaning pad, comprising:
    a first nonwoven layer formed of a blend of polypropylene fibers and rayon fibers and having an inner surface and an absorbent outer surface;
    a second nonwoven layer formed of polyester spunbond continuous filaments, said second layer having an inner surface laminated to the inner surface of the first layer, the second layer defining an exposed outer surface; and
    a plurality of abrasive formations of thermoplastic polymer melt-adhered to the exposed outer surface of the second layer and defining discrete protuberances on the exposed surface of the second layer.

2. A cleaning pad according to claim 1, wherein the thermoplastic polymer is polyester.

3. A cleaning pad according to claim 1, wherein the abrasive polymer formations are arranged in a uniform pattern of discrete spaced apart polymer beads adhered to the exposed surface of the second layer.

4. A cleaning pad according to claim 1, wherein the polypropylene and rayon fibers are bonded to one another at discrete points according to a predetermined pattern.

5. A cleaning pad according to claim 1, wherein the second layer comprises a polyester nonwoven web of trilobal filaments having a basis weight of at least about 2.0 oz./yd$^2$.

6. A cleaning pad according to claim 5, wherein the nonwoven web of said second layer has a basis weight of about 2.9 oz/yd$^2$.

7. A cleaning pad according to claim 1, further comprising an adhesive layer interposed between the first nonwoven layer and the second nonwoven layer adhesively laminating the second layer to the first layer.

8. A nonwoven composite cleaning pad, comprising:
    a first nonwoven layer having a thermal bonded nonwoven structure formed of a blend of polypropylene fibers and rayon fibers, said first nonwoven layer having an inner surface and an absorbent outer surface;
    a second nonwoven layer having an inner surface disposed in opposing face-to-face relation to the inner surface of the first layer, the second layer formed of polyester spunbond continuous filaments and defining an exposed outer surface;
    an adhesive layer disposed between the opposing inner surfaces of said first and second nonwoven layers bonding the layers together to form a composite nonwoven structure; and
    a plurality of abrasive formations of thermoplastic polymer melt-adhered to and projecting from the exposed outer surface of the second nonwoven layer.

9. A method of manufacturing a nonwoven composite, comprising:
    providing a first nonwoven polymeric layer having an inner surface and an absorbent outer surface;
    laminating one surface of a second nonwoven polymeric layer to the inner surface of the first layer such that the second layer defines an exposed outer surface; and
    applying molten thermoplastic polymer directly to the exposed outer surface of the second layer in a plurality of discrete locations and allowing the molten polymer to solidify to form a plurality of melt-adhered abrasive polymer formations.

10. A method according to claim 9, wherein the laminating step includes laminating to the first layer a second layer comprising filaments that are crimped and trilobal in shape and have a basis weight of at least about 2.0 oz/in$^2$.

11. A method according to claim 9, wherein the applying step includes transferring molten thermoplastic polymer to an applicator roll engraved with a uniform pattern of spaced apart indentations, directing the exposed surface of the second nonwoven layer into contact with the applicator roll, and transferring molten thermoplastic polymer present in the indentations to the second nonwoven layer to form a pattern of spaced apart polymer protuberances adhered to the exposed surface of the second layer.

12. A method of manufacturing a nonwoven composite, comprising:

providing a first nonwoven polymeric layer having a thermal bonded nonwoven structure formed of a blend of polypropylene fibers and rayon fibers, said first nonwoven layer having an inner surface and an absorbent outer surface;

laminating one surface of a second nonwoven polymeric layer to the inner surface of the first layer such that the second layer defines an exposed outer surface, wherein the second layer is formed of polyester spunbond continuous filaments; and applying molten thermoplastic polymer directly to the exposed outer surface of the second layer in a plurality of discrete locations and allowing the molten polymer to solidify to form a plurality of melt-adhered abrasive polymer formations.

* * * * *